United States Patent
Otsubo

(10) Patent No.: US 6,402,728 B2
(45) Date of Patent: Jun. 11, 2002

(54) DISPOSABLE DIAPER

(75) Inventor: Toshifumi Otsubo, Kagawa-ken (JP)

(73) Assignee: Uni-Charm Corporation (JP)

( * ) Notice: Subject to any disclaimer, the term of this patent is extended or adjusted under 35 U.S.C. 154(b) by 4 days.

(21) Appl. No.: 09/737,903

(22) Filed: Dec. 15, 2000

(30) Foreign Application Priority Data

Dec. 17, 1999 (JP) .......................................... 11-359082

(51) Int. Cl.⁷ ................................................ A61F 13/15
(52) U.S. Cl. ........................ 604/385.19; 604/385.01; 604/385.27; 604/358; 428/192
(58) Field of Search ................ 604/385.01, 385.27, 604/385.19, 358; 428/192

(56) References Cited

U.S. PATENT DOCUMENTS 4,500,316 A    2/1985   Damico 5,576,091 A  * 11/1996   Zajaczkowski ............. 428/192

FOREIGN PATENT DOCUMENTS

| EP | 0 585 904 A2 | 3/1994 |
|----|--------------|--------|
| GB | 2 329 842 A  | 4/1999 |
| JP | U 6-5614     | 1/1994 |
| JP | U 7-27524    | 5/1995 |
| WO | WO 97/17920  | 5/1997 |
| WO | WO 00/44326  | 8/2000 |

* cited by examiner

Primary Examiner—Amy Vanatta
Assistant Examiner—Angela J. Grayson
(74) Attorney, Agent, or Firm—Baker & Daniels

(57) ABSTRACT

A diaper includes a topsheet, a backsheet and a core disposed therebetween to define a front and rear waist regions and a crotch region. An elastic member surrounds a predetermined zone of the core about the vicinity of a longitudinal center line of the diaper. The plastic member is located in a rear half of the diaper and is secured under tension to the upper surface of the core so that the predetermined zone of the core is depressed downward to form a depression as the elastic member contracts.

9 Claims, 7 Drawing Sheets

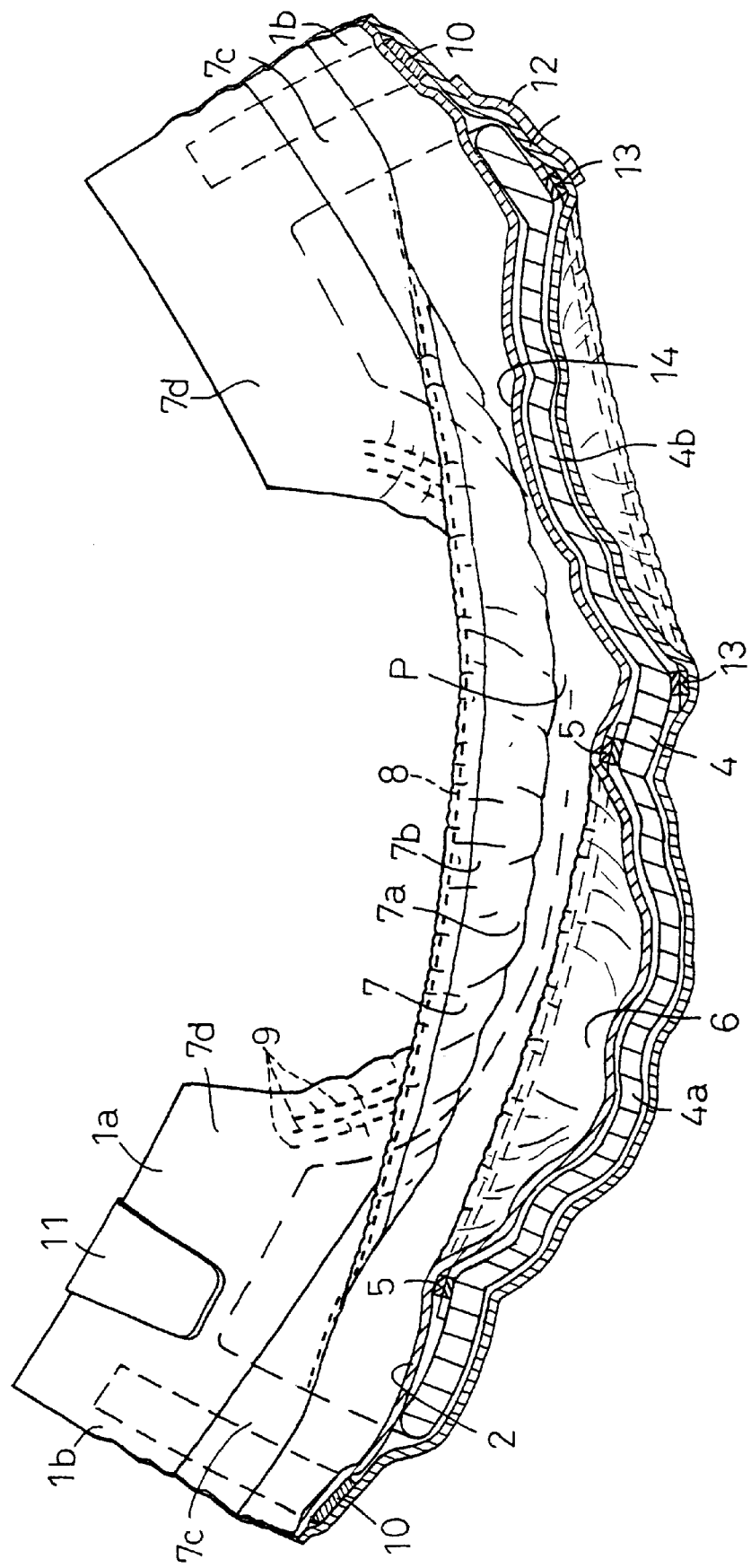

DISPOSABLE DIAPER

BACKGROUND OF THE INVENTION

This invention relates to a disposable diaper for absorbing and containing body wastes.

Japanese Utility Model Application Disclosure No. 1994-5614 describes a disposable diaper having a basic structure comprising a liquid-pervious topsheet, a liquid-impervious backsheet and a liquid-absorbent core disposed between these two sheets wherein the basic structure is formed in a zone adapted to be placed against the wearer's hip with a depression extending from the upper side to the lower side of the core to contain body wastes. The diaper described in the Application is effective to prevent leakage of body wastes by receiving and containing body wastes in the depression formed in the core.

Japanese Utility Model Application Disclosure No. 1993-27524 describes a disposable diaper comprising a liquid-pervious topsheet, a liquid-impervious backsheet and a liquid-absorbent core disposed between these two sheets. A pair of flaps extend longitudinally of the diaper across its front waist region and crotch region and a zone of the core lying between the flaps is formed with a protuberance extending upward from the upper surface of the core. The diaper described in the Application enables the wearer's penis to be placed against the protuberance and thereby enables discharged urine to be rapidly absorbed by the core.

SUMMARY OF THE INVENTION

An object of this invention is to provide a disposable diaper enabling the core to be formed in its predetermined zones with a depression and a protuberance without previously molding the core to form such depression and protuberance.

According to this invention, there is provided a disposable diaper contoured by transversely opposite side edges and longitudinally opposite ends and comprising a liquid-pervious topsheet, a liquid-impervious backsheet and a liquid-absorbent core having first and second surfaces and disposed between the topsheet and the backsheet to configure, longitudinally of the diaper, a front waist region, a rear waist region and a crotch region extending between the front and rear waist regions.

This invention further comprises an elastic member that is placed on and secured under tension to the first surface of the core to surround a predetermined zone spaced inward from the transversely opposite side edges and the longitudinally opposite side ends so that the predetermined zone of the core is curved toward the second surface of the core as the elastic member contracts against the rigidity of the core.

This invention includes the following embodiments.

The elastic member surrounds the predetermined zone of the core about the vicinity of a longitudinal center line bisecting a dimension between the transversely opposite side edges of the diaper and such elastic member is placed in at least one of a front half of the diaper extending from the vicinity of a transverse center line bisecting a dimension between the longitudinally opposite ends of the diaper to the end of the front waist region and a rear half of the diaper extending from the vicinity of the transverse center line to the end of the rear waist region.

The elastic member is placed in both the front half and rear half of the diaper so that the elastic member surrounds a first predetermined zone on the second surface of the core in the front half and curves the first predetermined zone on the second surface toward the first surface to form a protuberance while the elastic member surrounds a second predetermined zone on the first surface of the core in the rear half and curves the second predetermined zone on the first surface toward the second surface to form a depression.

The elastic member is placed in both the front half and rear half of the diaper so that the elastic members surround respective predetermined zones on the first surface of the core and curve the respective predetermined zones in the first half and second half toward the second surface to form depressions, respectively.

The core is thinner in the predetermined zones of the core surrounded by the respective elastic members than in the remaining zone of the core not surrounded by the respective elastic members.

BRIEF DESCRIPTION OF THE DRAWINGS

FIG. 7 is a sectional view taken along line D—D in FIG. 6.

DETAILED DESCRIPTION OF THE PREFERRED EMBODIMENTS

Details of a disposable diaper according to this invention will be more fully understood from the description given hereunder with reference to the accompanying drawings.

Figure 1:
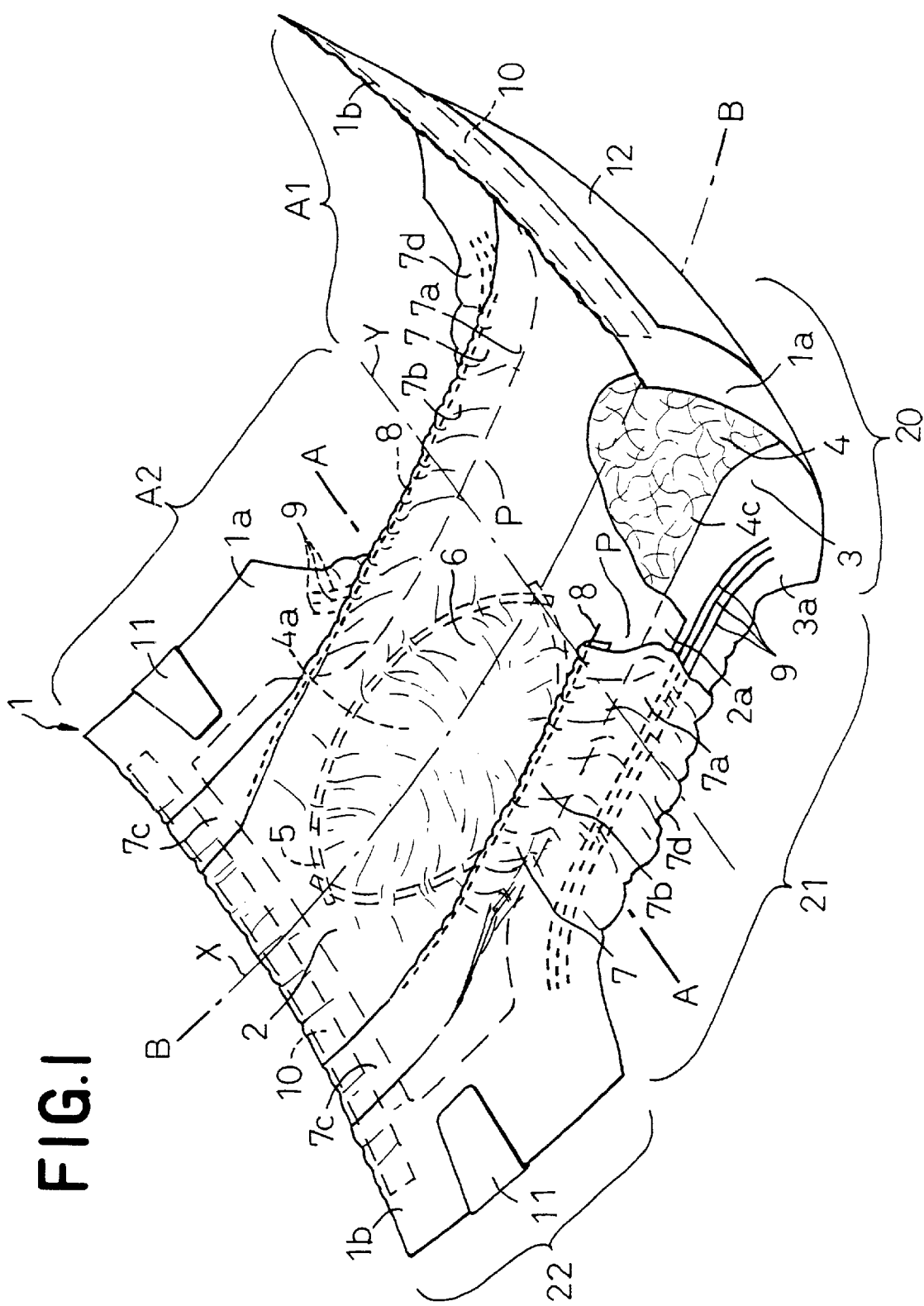
FIG. 1 is a perspective view showing one embodiment of a partially cutaway disposable diaper according to this invention.
Figure 2:
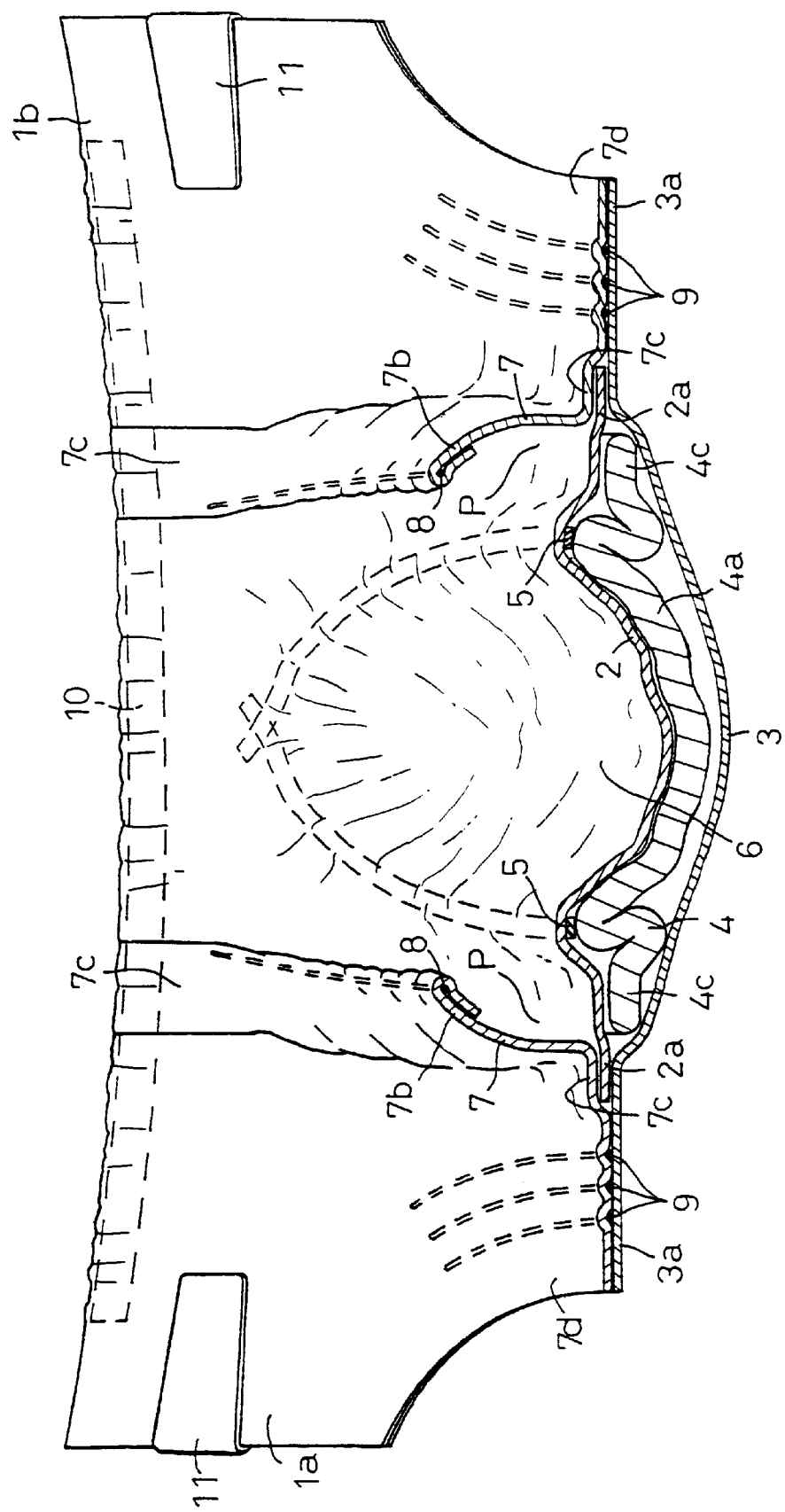
FIG. 2 is a sectional view taken along line A—A in FIG. 1.
Figure 3:
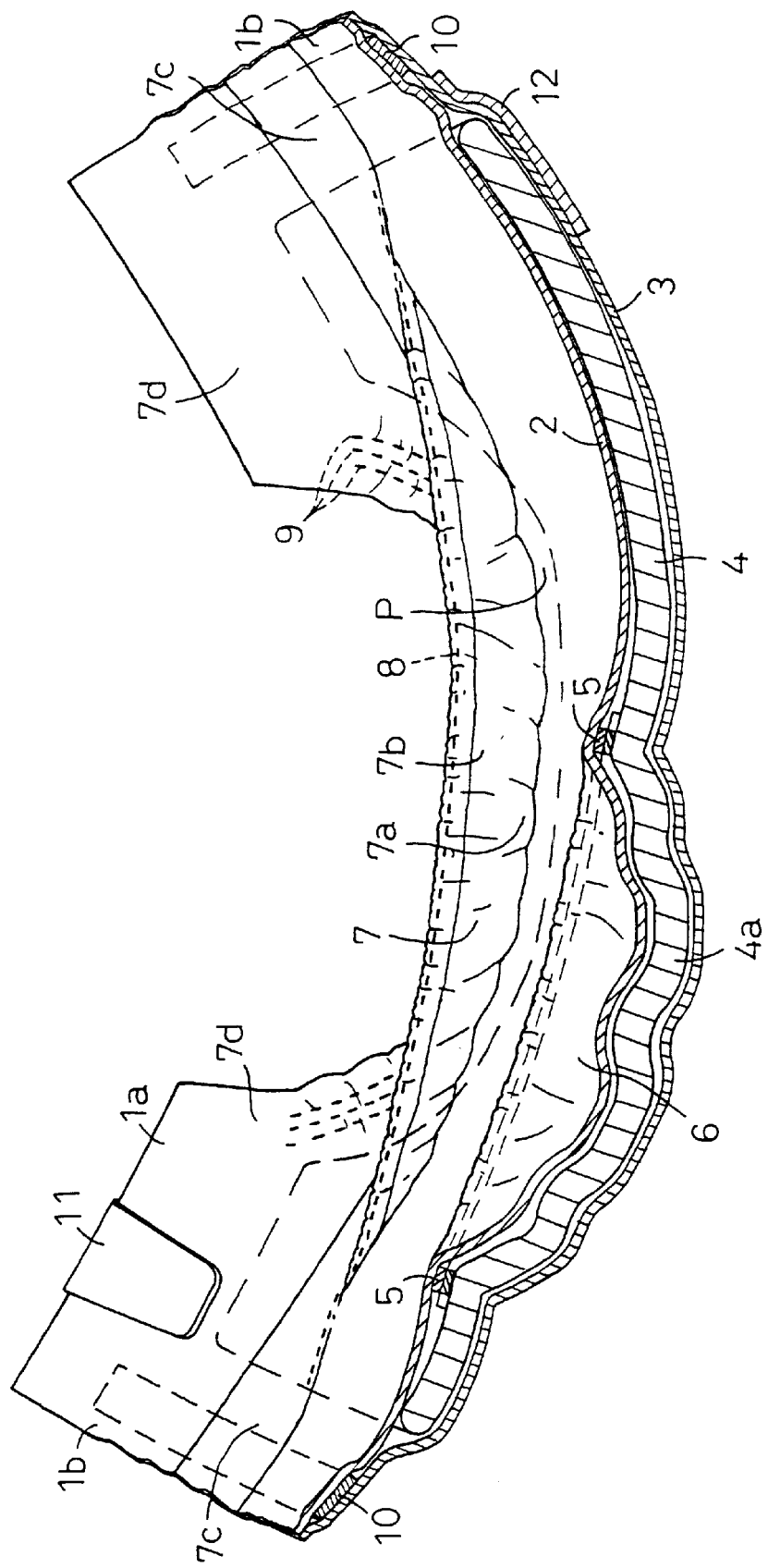
FIG. 3 is a sectional view taken along line B—B in FIG. 1.

FIG. 1 is a perspective view showing one embodiment of a partially cutaway disposable diaper according to this invention, FIG. 2 is a sectional view taken along line A—A in FIG. 1 and 3 is a sectional view taken along line B—B in FIG. 1. The diaper 1 basically comprises a liquid-pervious topsheet 2, a liquid-impervious backsheet 3 and a liquid-absorbent core 4 disposed between the top- and backsheets 2, 3 and bonded to the inner surface of at least one of the top- and backsheets 2, 3. The diaper 1 is longitudinally configured by a front waist region 20, a rear waist region 22 and a crotch region 21 extending between these front and rear waist regions 20, 22. The diaper 1 is contoured by transversely opposite side edges 1a extending in parallel to each other longitudinally of the diaper 1 and, in the crotch region 21, curving inwardly of the diaper 1 to describe circular arcs and longitudinally opposite ends 1b extending in parallel to each other transversely of the diaper 1. The diaper 1 is further provided in the vicinity of transversely opposite side edges 4c of the core 4 with a pair of barrier cuffs 7 extending longitudinally of the diaper 1.

The diaper 1 is further provided in its rear half zone A2 extending from the vicinity of a transverse center line Y bisecting a dimension between the longitudinally opposite ends 1b of the diaper 1 to the vicinity of the end 1b of the rear waist region 22 with elastic member 5 extending to surround a predetermined zone of the core 4.

The elastic member 5 extends between the lower surface of the topsheet 2 and the inner surface of the core 4 annularly about the vicinity of a longitudinal center line X bisecting a dimension between the transversely opposite side edges 1a of the diaper 1 and secured under tension to the inner surface of the topsheet 2 and the upper surface of the core 4. The elastic member 5 is contractable against a rigidity of the core 4 so that the zone 4a of the core 4 surrounded by the elastic member 5 may be contracted inwardly of the annulus defined by the elastic member 5 as the latter contracts.

The zone 4a of the core 4 becomes depressed downwardly of the diaper 1 to form a depression 6 as the zone 4a is contracted inwardly of the annulus of the elastic member 5. The depression 6 is formed in the rear half A2 of the diaper 1 covering a wearer's hip and able to receive and contain discharged body wastes which are then absorbed by the core 4 through the topsheet 2.

The barrier cuffs 7 comprise fixed portions 7a extending longitudinally of the diaper 1 and bonded to transversely opposite side edge portions 2a of the topsheet 2 lying immediately outside transversely opposite side edges 4c of the core 4, free side portions 7b extending inward transversely of the diaper 1 in the crotch region 21 and normally biased to rise on the diaper 1 and longitudinally opposite end portions 7c collapsed inward transversely of the diaper 1 and bonded in such collapsed state to the topsheet 2 at the longitudinally opposite end portions 1b of the diaper 1, respectively. The respective free side portions 7b of the cuffs 7 are provided along the vicinity of their respective edges with elastic members 8 secured under tension thereto and covered with portions of the respective free side portions 7b.

Along the opposite side edge portions 1a of the diaper 1, elastic members 9 associated with leg-holes are disposed between transversely opposite side edge portions 3a of the backsheet 3 and respective outer side edge portions 7d extending outward transversely of the diaper 1 from the respective fixed portions 7a of the cuffs 7 and secured under tension to the inner surfaces of the side edge portions 3a of the backsheet 3 and/or of the outer side edge portions 7d of the cuffs 7.

Along the longitudinally opposite end portions 1b of the diaper 1, film-like elastic members 10 associated with a waist-hole extend between the top- and backsheets 2, 3 and secured under tension to the inner surface at least one of these two sheets 2, 3. In the rear waist region 22, the side edge portions 1a of the diaper 1 are provided with tape fasteners 11 having their proximal end portions attached to the respective side edge portions 1a and extending inward transversely of the diaper 1. On the other hand, in the front waist region 20 of the diaper 1, a strip of rectangular target tape 12 is attached to the outer surface of the backsheet 3 so that the tape fasteners 11 may be anchored on the strip of target tape 12.

As will be seen in FIG. 2, the transversely opposite side edge portions 2a of the topsheet 2 terminate immediately outside the transversely opposite side edges 4c of the core 4 and the transversely opposite side edge portions 3a of the backsheet 3 as well as the outer side edge portions 7d of the cuffs 7 extend outward beyond the side edge portions 2a of the topsheet 2 transversely of the diaper 1. In the vicinity of the respective side edge portions 1a of the diaper 1, the respective side edge portions 2a, 3a, 7d of the top- and backsheets 2, 3 and the cuffs 7 are placed upon and bonded to one another.

Referring to FIG. 1, gathers are formed along the transversely opposite side edge portions 1a as well as the longitudinally opposite end portions 1b of the diaper 1 and along the free side portions 7b of the cuffs 7 as the elastic members 9 associated with the leg-holes, the elastic members 10 associated with the waist-hole and the elastic members 8 attached to the free side portions 7b of the cuffs 7 are relieved of tension. The diaper 1 is longitudinally curved thereupon with its inner surface inside and contraction of the elastic members 8 attached to the free side edge portions 7b of the cuffs 7 causes these free side edge portions 7b to rise on the inner surface of the diaper 1. The free side edge portions 7b cooperate with the topsheet 2 to form pockets P opening inward transversely of the diaper 1.

Free end portions of the respective tape fasteners 11 may be anchored on the strip of target tape 12 by means of pressure-sensitive adhesive (not shown) applied on the inner surfaces of these free end portions to form the pair of leg-holes and the waist-hole (both not shown).

Figure 4:
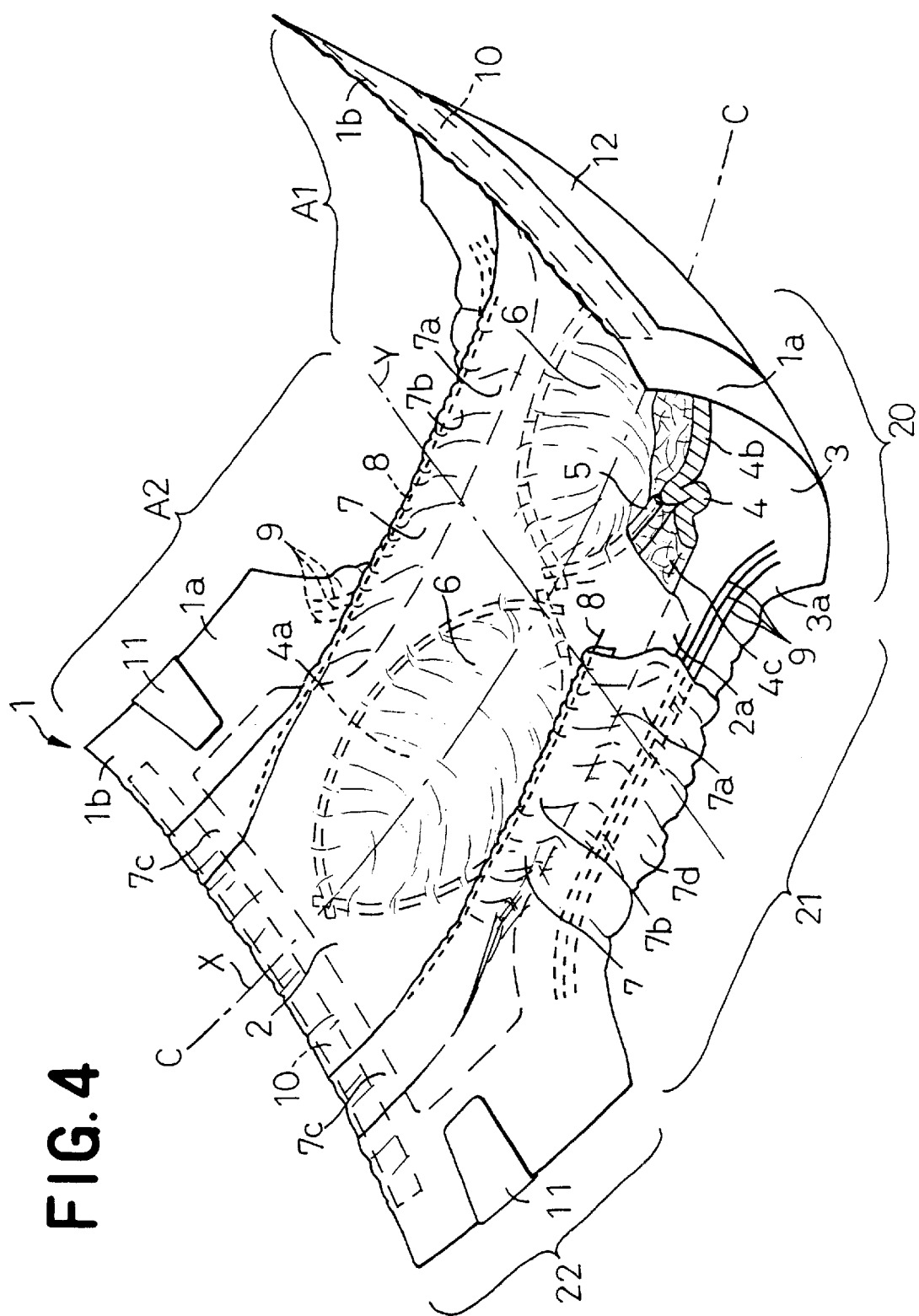
FIG. 4 is a view similar to FIG. 1 showing another embodiment of the diaper.
Figure 5:
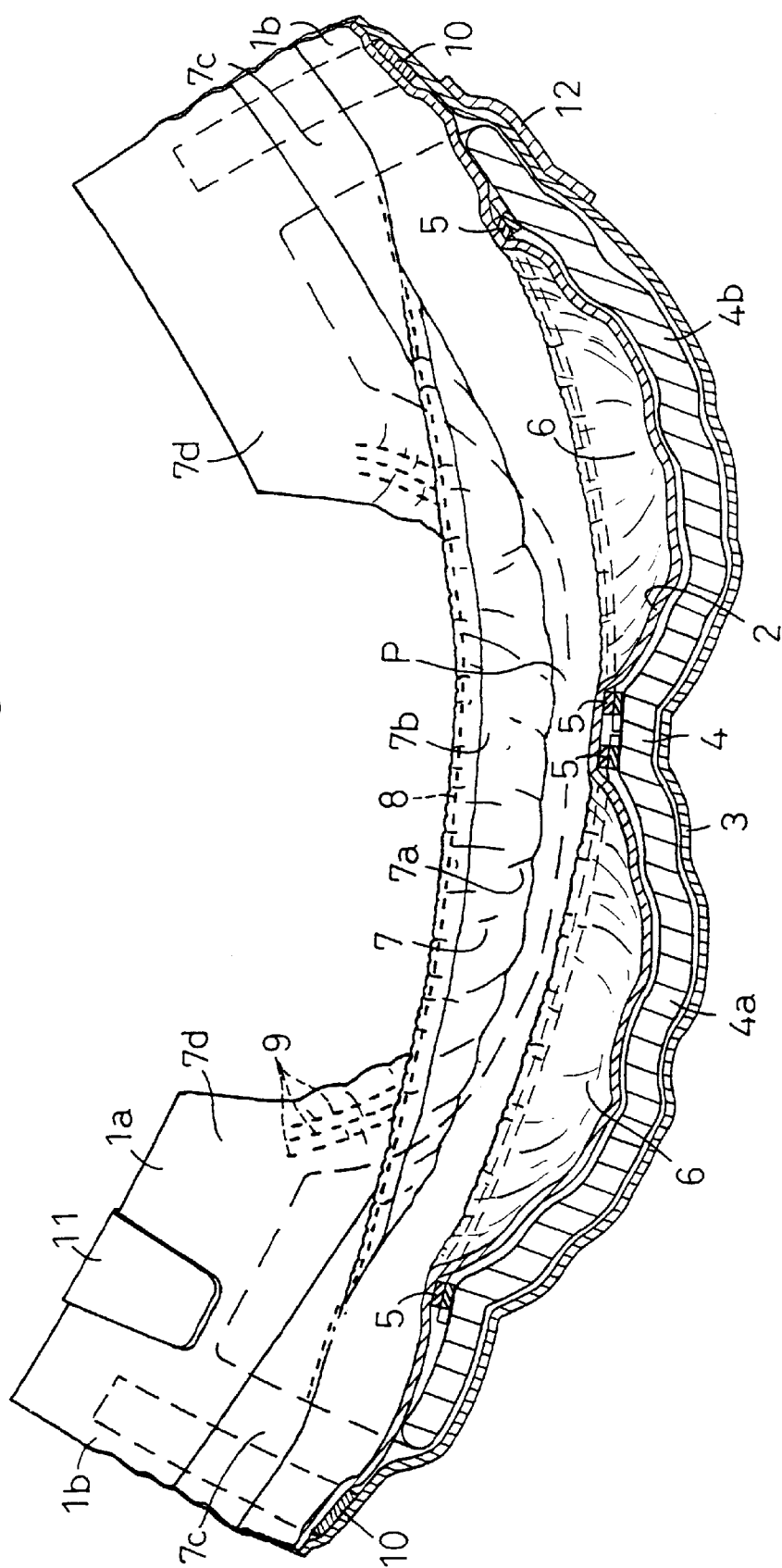
FIG. 5 is a sectional view taken along line C—C in FIG. 4.

FIG. 4 is a view similar to FIG. 1 showing another embodiment of the diaper and FIG. 5 is a sectional view taken along line C—C in FIG. 4. The diaper 1 according to this embodiment is similar to that of FIG. 1 in that the core 4 is disposed between the top- and backsheets 2, 3 and the diaper 1 is longitudinally configured by the front and rear waist regions 20, 22 and the crotch region 21 extending between these two waist regions 20, 22. The diaper 1 according to this embodiment also has the transversely opposite side edge portions 1a, the longitudinally opposite end portions 1b and the pair of barrier cuffs 7 normally biased to rise on the inner surface of the diaper 1.

The diaper 1 is further provided in its front and rear half zone A1, A2 extending from the vicinity of a transverse center line Y bisecting a dimension between the longitudinally opposite ends 1b of the diaper 1 to the vicinity of the respective ends 1b of the diaper 1 with elastic members 5 extending to surround predetermined zones of the core 4, respectively. The respective elastic members 5 extend annularly about the vicinity of the longitudinal center line X between the topsheet 2 and the core 4 and secured under tension to said inner surface of the topsheet 2 and the upper surface of the core 4. The elastic members 5 are contractable against a rigidity of the core 4 so that the zones 4a, 4b of the core 4 surrounded by the respective elastic members 5 may be contracted inwardly of the annuli defined by the elastic members 5 as the latter contract.

The zones 4a, 4b of the core 4 lying in the front and rear halves A1, A2 of the diaper 1 become depressed downwardly of the diaper 1 to form a depressions 6 as the zones 4a, 4b are contracted inwardly of the annuli defined by the elastic members 5. The diaper 1 of FIG. 4 is particularly suitable as men's diaper since the depression 6 is formed also in the front half A1 of the diaper 1 and wearer's penis can be received in this depression 6.

Figure 6:
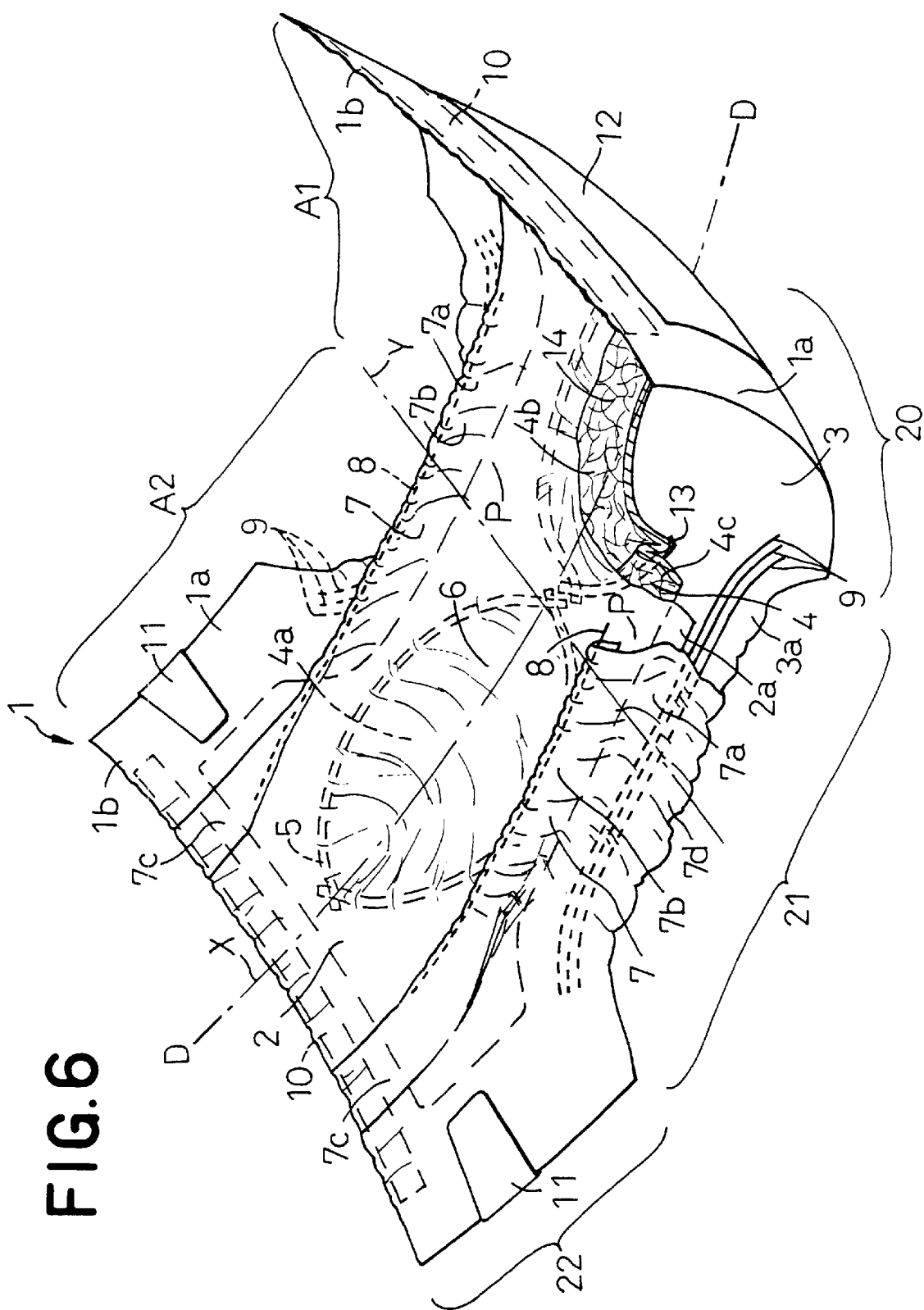
FIG. 6 is a view similar to FIGS. 1 and 4 showing still another embodiment of the diaper.

FIG. 6 is a view similar to FIGS. 1 and 4 showing still another embodiment of the diaper and FIG. 7 is a sectional view taken along line D—D in FIG. 6. The diaper 1 according to this embodiment is similar to those shown in FIGS. 1–4 in that the diaper 1 comprises the top- and backsheets 2, 3 and the core 4 disposed between these two sheets 2, 3 so as to configure, as viewed longitudinally of the diaper 1, the front and rear waist regions 20, 22 and the crotch region 21 extending between these two waist regions 20, 22. The diaper 1 according to this embodiment also has the transversely opposite side edge portions 1a, the longitudinally opposite end portions 1b and the pair of barrier cuffs 7 normally biased to rise on the inner surface of the diaper 1.

The diaper 1 is provided in its front and rear half zones A1, A2 with elastic members 13, 5 surrounding predetermined zones of the core 4, respectively. The respective elastic members 5, 13 extend annularly about the vicinity of the longitudinal center line X. The elastic member 13 lying in the front half A1 is disposed between the lower surface of the core 4 and the backsheet 3 and secured under tension to the lower surface of the core 4 and the inner surface of the backsheet 3. The elastic member 5 lying in the rear half A2 disposed between the upper surface of the core 4 and the inner surface of the topsheet 2 and secured under tension to the inner surface of the topsheet 2 and the upper surface of the core 4.

The core 4 is thinner in the zones 4a, 4b of the core 4 surrounded by the elastic members 5, 13, respectively, than in the remaining zone extending outside these elastic members 5, 13. Correspondingly, the zones 4a, 4b are less stiff than the remaining zone extending outside the elastic members 5, 13. Such local difference in the thickness as well as the rigidity of the core 4 facilitates the zones 4a, 4b of the core 4 to contract inward from the annuli defined by the respective elastic members 5, 13.

The elastic members 5, 13 are contractable against a rigidity of the core 4 so that the zones 4a, 4b of the core 4 surrounded by the respective elastic members 5, 13 may be contracted inwardly of the annuli defined by said elastic members 5, 13 as the latter contract.

In the front half A1 of the diaper 1, the zone 4b of the core 4 protrudes upwardly of the diaper 1 as the zone 4b contracts inward from the annulus defined by the elastic member 13 to form a protuberance 14 in this zone 4b of the core 4. In the rear half A2 of the diaper 1, on the other hand, the zone 4a of the core 4 is depressed downwardly of the diaper 1 as the zone 4a contracts inward from the annulus defined by the elastic member 13 to form the depression 6 in the zone 4a of the core 4. The diaper 1 of FIG. 6 is particularly suitable as women's diaper since the diaper 1 is formed in its front half A1 with the protuberance 14 adapted to be placed against wearer's vulva.

This embodiment of the diaper 1 may be modified so that a pair of elastic members 13 are provided in the front and rear half zones A1, A2 both annularly extending on the lower surface of the core 4 and secured under tension to the inner surface of the backsheet 3 and the lower surface of the core 4. According to this variant, the zones 4a, 4b of the core 4 surrounded by the respective elastic members 13 in the front and rear halves A1, A2 of the diaper 1 protrude upwardly of the diaper 1 to form respective protuberances 14. The protuberance 14 formed in the rear half A2 of the diaper 1 is adapted to be placed against the wearer's hip and, therefore, the diaper 1 according to such variant is particularly suitable for baby's diaper normally discharging loose passage.

An alternative arrangement is also possible without departing from the scope of this invention such that only the front half A1 of the diaper 1 is formed with the depression 6 or the protuberance 14 or only the rear half A2 of the diaper 1 is formed with the protuberance 14. It is also possible without departing from the scope of this invention to form the depression 6 only in the front half A1 of the diaper 1 to form the protuberance 14 only in the rear half A2 of the diaper 1. It is essential that the elastic member 5 is bonded to at least the upper surface of the core 4 and the elastic member 13 is bonded at least to the lower surface of the core 4. It is not essential to secure these elastic members 5, 13 to both the topsheet and the backsheet 3.

The topsheet 2 is formed by a liquid-pervious nonwoven fabric or a porous plastic film, preferably by a liquid-pervious hydrophilic sheet. The backsheet 3 is formed by a hydrophobic nonwoven fabric, a liquid-impervious plastic film, a laminated sheet of these hydrophobic nonwoven fabric and plastic film, preferably by a breathable liquid-impervious sheet. The cuffs 7 are formed by a hydrophobic nonwoven fabric, preferably by a breathable liquid-impervious sheet.

The nonwoven fabric used for those purposes may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The composite nonwoven fabric (SMS nonwoven fabric) consisting of a melt blown nonwoven fabric having a high water-resistance sandwiched between two layers of a spun bond nonwoven fabric being in strength as well as in flexibility may be used. The SMS nonwoven fabric can be made by a process comprising the steps of sandwiching the melt blown nonwoven fabric with the two layers of spun bond nonwoven fabric and then bonding these melt blown nonwoven fabric and the spun bond nonwoven fabric together using a pressing technique. Component fibers of the nonwoven fabric may be selected from a group including polyolefine-, polyester- and polyamide-fibers, and conjugated fiber of polyethylene/polypropylene or polyester and the like.

The core 4 is a mixture of fluff pulp and high absorption polymer particles compressed in to a desired thickness and entirely covered with a water-pervious sheet (not shown) such as tissue paper. Bonding of the core 4, the elastic members 5, 8, 9, 10, 13, the sheets 2, 3 and the cuffs 7 may be carried out using adhesive such as hot melt adhesive or pressure-sensitive adhesive or a heat-sealing technique.

The disposable diaper according to this invention enables the depression and/or the protuberance to be formed in the core without previously molding the core to form such depression and/or protuberance. More specifically, the core is provided on its upper and/or lower surfaces with the elastic member to surround a predetermined zone of the core and the elastic member is secured under tension to the upper and/lower surfaces of the core so that the zone of the core surrounded by the elastic member may contract inwardly of the elastic member to form the depression extending downwardly and/or the protuberance extending upwardly of the diaper as the elastic member contracts.

The diaper formed in its rear half with the depression will be effective to prevent leakage of body wastes from the diaper by reliably containing the discharged body wastes in the depression. The diaper formed in its front half with the depression is particularly suitable as men's diaper since the wearer's penis can be held in this depression. The diaper formed in its front half with the protuberance is particularly suitable as women's diaper since this protuberance is adapted to be placed against the wearer's vulva and thereby facilitates the discharged urine to be absorbed by the core.

What is claimed is:

1. A disposable diaper contoured by transversely opposite side edges and longitudinally opposite ends which comprises:
    a liquid-pervious topsheet;
    a liquid-impervious backsheet;
    a liquid-absorbent core having first and second surfaces and disposed between said liquid-pervious topsheet and said liquid-pervious backsheet;

a front waist region;

a rear waist region;

a crotch region extending between said front and rear waist regions; and an elastic member placed on and secured under tension to said first surface of said liquid-absorbent core and surrounding a zone of the liquid-absorbent core that is spaced inward from both said transversely opposite side edges and said longitudinally opposite side ends, said zone of said liquid-absorbent core being curved toward said second surface of said liquid-absorbent core as said elastic member contracts against a rigidity of said liquid-absorbent core.

2. The diaper according to claim 1, wherein said elastic member surrounds said zone of said liquid-absrobent core about a vicinity of a longitudinal center line which bisects a dimension between said transversely opposite side edges of said diaper and said elastic member is placed in at least one of a front half of said diaper extending from a vicinity of a transverse center line bisecting a dimension between said longitudinally opposite ends of said diaper to an end of said front waist region and a rear half of said diaper extending from a vicinity of said transverse center line to an end of said rear waist region.

3. The diaper according to claim 1, wherein said elastic member comprises elastic members that are placed in both a front half and a rear half of said diaper so that an elastic member surrounds a first zone on said second surface of said liquid-absorbent core in said front half and deforms said first zone on said second surface toward said first surface to form a protuberance, and an elastic member surrounds a second zone on said first surface of said liquid-absorbent core in said rear half and deforms said second zone on said first surf are toward said second surface to form a depression.

4. The diaper according to claim 1, wherein said elastic member is positioned in both a front half and a rear half of said diaper so that respective portions of said elastic member surrounds zones on said first surface of said liquid-absorbent core in said front and rear half of said diaper and deform said zones in said front half and said rear half of said diaper toward said second surface to form depressions.

5. The diaper according to claim 1, wherein said liquid-absrobent core is thinner in said zone of said liquid-absorbent core that is surrounded by said elastic member than in a remaining portion of said liquid-absorbent core.

6. The diaper according to claim 1, wherein said elastic member comprises elastic members that are placed in both a front half and a rear half of said diaper so that an elastic member surrounds a first zone on said second surface of said liquid-absorbent core in said front half and deforms said first zone on said second surface toward said first surface to form a depression, and an elastic member surrounds a second zone on said first surface of said liquid-absorbent core in said rear half and deforms said second zone on said first surf are toward said second surface to form a depression.

7. The diaper according to claim 2, wherein said liquid-absorbent core is thinner in said zone of said liquid-absorbent core that is surrounded by said elastic member than in a remaining portion of said liquid-absorbent core.

8. The diaper according to claim 3, wherein saied liquid-absorbent core is thinner in each of said first and second zones of said liquid-absorbent core that are surrounded by said elastic members than in a remaining portion of said liquid-absorbent core.

9. The diaper according to claim 4, wherein said liquid-absorbent core is thinner in said zones of said liquid-absorbent core that are surrounded by said elastic member than in a remaining portion of said liquid-absorbent core.

* * * * *